United States Patent [19]

Kimura et al.

[11] Patent Number: 4,718,432

[45] Date of Patent: Jan. 12, 1988

[54] CT IMAGING APPARATUS AND METHOD FOR MEASURING LOCAL CEREBRAL BLOOD FLOW

[75] Inventors: Tokunori Kimura, Yaita; Naotoshi Kobayashi, Kawasaki, both of Japan

[73] Assignee: Kabushiki Kaisha Toshiba, Kawasaki, Japan

[21] Appl. No.: 15,491

[22] Filed: Feb. 6, 1987

Related U.S. Application Data

[63] Continuation of Ser. No. 746,523, Jun. 19, 1985, abandoned.

[30] Foreign Application Priority Data

Jun. 20, 1984 [JP] Japan ................................. 59-126734

[51] Int. Cl.⁴ ............................................. A61B 6/00
[52] U.S. Cl. .................................... 128/654; 128/659; 128/719; 250/303
[58] Field of Search ............... 128/653, 654, 659, 719, 128/730; 250/380, 303

[56] References Cited

U.S. PATENT DOCUMENTS

| | | | |
|---|---|---|---|
| 3,527,205 | 9/1970 | Jones .................................... | 128/719 |
| 3,890,959 | 6/1975 | Youdin et al. ....................... | 128/654 |
| 3,976,050 | 8/1976 | Glasser et al. ....................... | 128/654 |
| 4,141,347 | 2/1979 | Green et al. ......................... | 128/663 |
| 4,205,687 | 6/1980 | White et al. ......................... | 128/663 |
| 4,233,842 | 11/1980 | Raemer et al. ...................... | 128/719 |

FOREIGN PATENT DOCUMENTS

| | | | |
|---|---|---|---|
| 2418786 | 10/1974 | Fed. Rep. of Germany ...... | 128/654 |
| 2035748 | 6/1980 | United Kingdom ................ | 128/659 |

OTHER PUBLICATIONS

Anderson et al., "An Automated Cerebral Blood Flow Analyzer", Journal of Nuclear Medicine, vol. 18, No. 7, Jul. 1977, pp. 728–731.

Seylaz et al., "Analytical Problems Associated with the Non-Invasive Measurements of Cerebral Blood Flow in Cerebrovascular Diseases", Medical & Biological Engineering and Computing, Jan. 1980, pp. 39–47.

"Mapping Local Blood Flow of Human Brain by CT Scanning During Stable Xenon Inhalation", Stroke, vol. 12, No. 4, Jul.-Aug. 1981, pp. 426, 436, by Meyer et al.

"Extracranial/Intracranial Surgery Guided by Xenon-CT Blood Flow Mapping", Abstract of a paper, 1984 Annual Meeting American Society of Neuroradiology by Teeter, Colsher et al.

Meyer et al., "Local Cerebral Blood Flow Measured by CT After Stable Xenon Inhalation", AJNR 1, pp. 213-223, May/Jun. 1980.

Kanno et al., "Two Methods for Calculating Regional Cerebral Blood Flow from Emmission Computed Tomography of Inert Gas Concentrations", Journal of Computer Assisted Tomography, 3(1), pp. 71–76, Feb. 1979.

*Primary Examiner*—William E. Kamm
*Assistant Examiner*—Ruth S. Smith
*Attorney, Agent, or Firm*—Finnegan, Henderson, Farabow, Garrett & Dunner

[57] ABSTRACT

In a CT imaging apparatus, tracer gas such as Xenon is drawn via a pipe into a patient in synchronism with X-ray tomographic data acquisition. The tracer gas inhalation is controlled by a data acquisition controller through a valve driver. The tracer gas concentrations in the local cerebral tissue and air expired from the patient are measured in the image analysis device. The first-mentioned tracer gas concentration is measured before its saturation in the patient. The partition coefficients of the local cerebral portions are calculated in the calculation device from the ratio of the first area to the second area. The first area is defined by the first curve representing the tracer gas concentration of the local cerebral tissue, while the second area is defined by the second curve representing the tracer gas concentration of the air expired by the patient.

5 Claims, 4 Drawing Figures

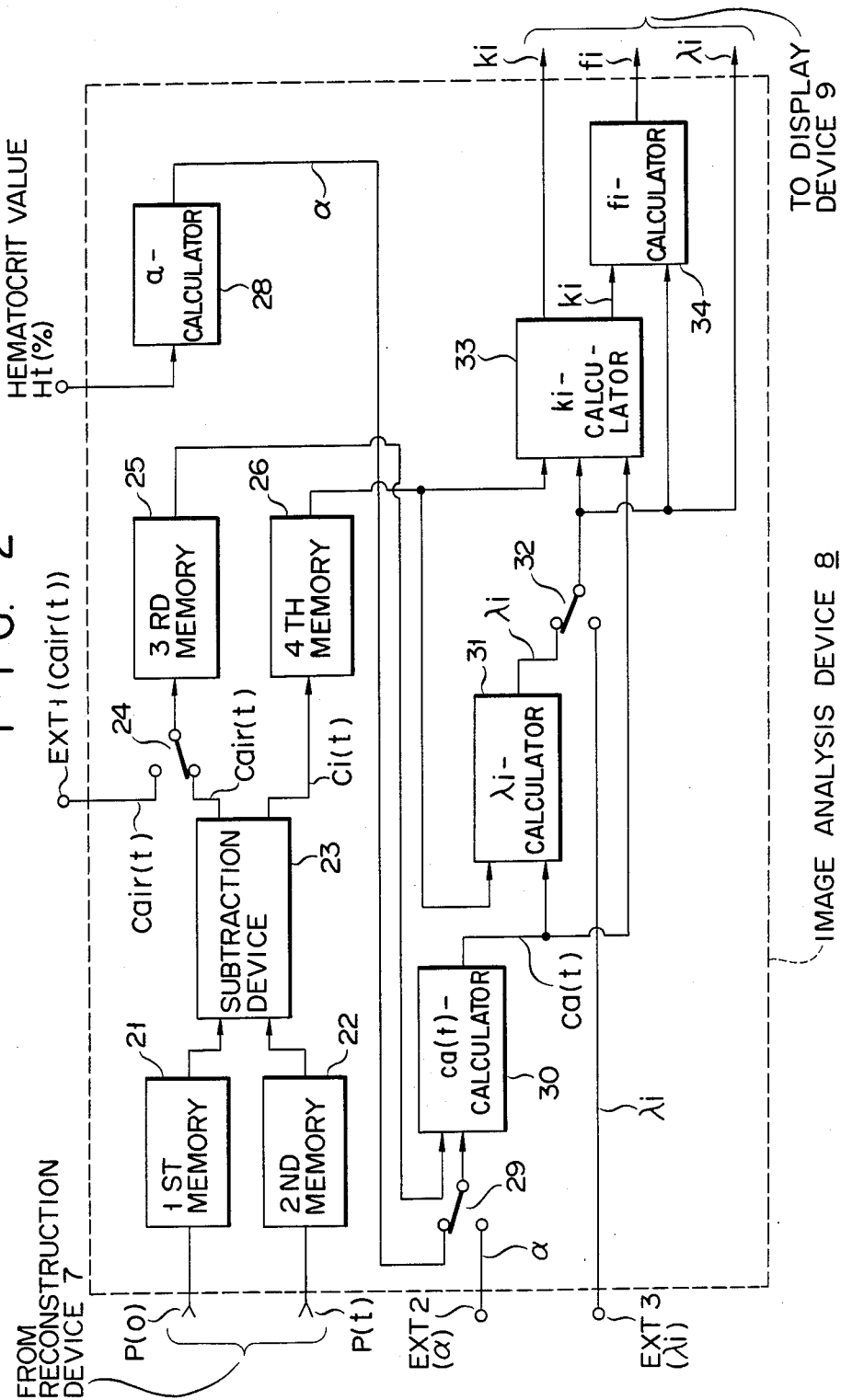
F I G. 2

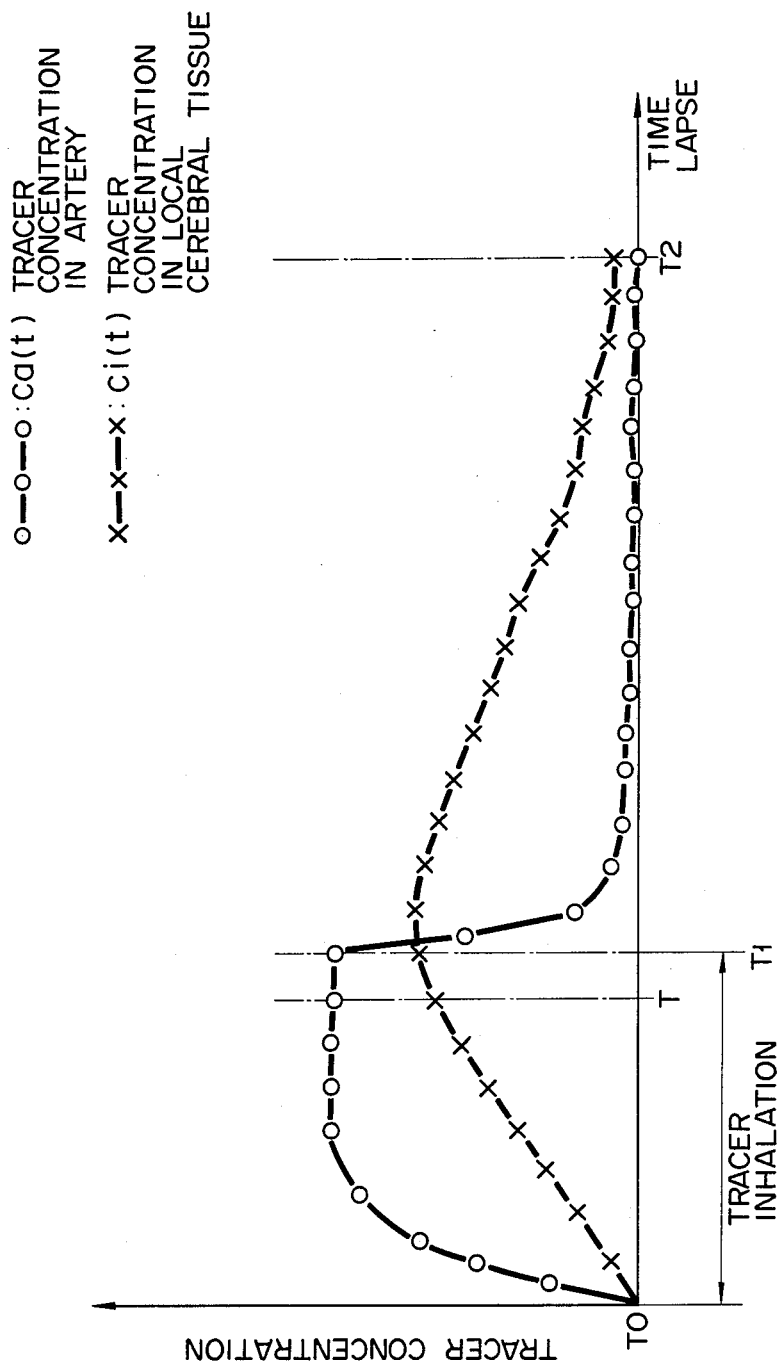

4,718,432

CT IMAGING APPARATUS AND METHOD FOR MEASURING LOCAL CEREBRAL BLOOD FLOW

This application is a continuation of application Ser. No. 746,523, filed June 19, 1985, now abandoned.

BACKGROUND OF THE INVENTION

1. Field of the Invention

The present invention relates to a CT (computerized tomography) imaging apparatus and related method for measuring local cerebral blood flow in which the local cerebral blood flow is detected by inhaling a tracer such as Xenon or Krypton into a patient under examination within a short time period and by employing an X-ray CT imaging apparatus.

2. Description of the Prior Art

A new non-invasive technique of cerebral blood flow measurement is recently known in the field, e.g., Radiology "Imaging of Xenon-enhanced cerebral blood flow with high resolution CT" issued in October, 1984 to Teeter and Colsher.

Conventionally, measurement of local cerebral blood flow is generally performed in the following manner.

A predetermined slice of the head of a patient under examination is scanned plurally over time during tracer inhalation so as to obtain tomographic images. A time-lapse variation of tracer concentration in cerebral regional tissue (to be referred to as Ci(t) hereinafter) and a time-lapse variation of tracer concentration in an artery (to be referred to as Ca(t) hereinafter) are obtained based on the obtained tomographic images.

Cerebral blood flow parameters, i.e., λi (partition coefficient), ki (build up rate) and fi (blood flow rate) are calculated based on the obtained variations Ci(t) and Ca(t) by the following equation (Kety-Schmidt equation) in accordance with the Fick principle:

$$Ci(T) = \lambda i \cdot ki \int_0^T Ca(t) \cdot \exp[-ki(T - t)]dt \quad (1)$$

or $$(d/dt)Ci(t) = ki\{\lambda i \cdot Ca(t) - Ci(t)\} \quad (1')$$

where Ci(T): tracer concentration of tissue i at time instance T

The above method uses a build up curve during tracer inhalation to obtain variations Ca(t) and Ci(t). For this reason, in order to obtain the correct values of the parameters λi, ki and fi, particularly, the partition coefficient λi of white matter, a tracer inhalation time of as long as 20 to 30 minutes is required. When the tracer inhalation time is long, the tracer cost is increased, a load on a patient under examination and an operator is increased, and the carbon dioxide gas content in blood of the patient under examination ($PaCO_2$) is increased. In addition, the blood flow rate of the patient under examination is reduced from a normal level due to anesthetic effects of the tracer.

The variation Ca(t) is normally obtained by monitoring the tracer concentration in expiratory gas. When the variation Ca(t) is converted into a value according to the scale of the variation Ci(t), arterial blood must be sampled at least twice before tracer inhalation and twice after tracer saturation. This method cannot therefore be a non-invasive examination in a strict sense, and the operation procedures are complex.

Recently, cerebral blood flow measurement has become indispensable to diagnosis of neurotic diseases, selection of therapy, and assessment of therapeutic effect. However, as described above, the conventional measurement method is difficult to perform and provides only a low precision, resulting in an impractical method.

It is an object of the present invention to provide a CT imaging apparatus for measuring local cerebral blood flow which can obtain cerebral blood flow parameters with high precision within a short tracer inhalation time and without requiring blood sampling.

SUMMARY OF THE INVENTION

These objects may be accomplished by providing a CT imaging apparatus for measuring local cerebral blood flow comprising:

a source of tracer gas;

a conducting member;

a tracer gas conducting member for supplying the tracer gas via the conducting member into the patient under examination;

means for controlling starting and ending times of supplying of the tracer gas;

means, including at least an X-ray generation source, a data acquisition device and an image reconstruction device, for simultaneously producing X-ray tomographic image data of preselected slices in both the patient and the conducting member, with the tomographic image data involving local cerebral blood flow in the patient and also tracer gas flow through the conducting member;

means for analyzing the reconstructed tomographic image data involving the local cerebral blood flow and the tracer gas flow so as to measure the local cerebral blood flow and the tracer gas blood flow; and means for displaying a reconstructed tomographic image obtained from the tomographic image data and for displaying an image indicating the measured local cerebral blood flow of the patient.

BRIEF DESCRIPTION OF THE DRAWINGS

These and other objects and features of the invention will become apparent with reference to the following specification and to the drawings in which:

FIG. 2 is a block diagram of the image analysis device of FIG. 1;

FIG. 4 is a graphic representation of tracer concentration measured by the apparatus shown in FIG. 1.

DETAILED DESCRIPTION OF THE PREFERRED EMBODIMENTS

Before describing the preferred embodiments of the present invention, the principle of the present invention will be summarized.

As described earlier, in order to correctly obtain the local cerebral blood flow, cerebral blood flow parameters, i.e., partition coefficient λi, build up rate ki, and blood flow rate fi must be measured correctly. As another condition, inhalation of a tracer gas must be terminated within a short time period.

In view of this, the present inventors established the so-called area method, i.e., a method of obtaining a partition coefficient λi given below:

$$\lambda i = \left( \int_0^{T2} Ci(t)dt \right) / \left( \int_0^{T2} Ca(t)dt \right)$$

where T2 is a time in which the tracer concentration becomes substantially zero and which is determined in association with a predetermined tracer inhalation time T1.

The coefficient λi is obtained by expressing the rate of change in tracer concentration at a given tissue region in terms of an area and obtaining the ratio of an area of the rate of change in tracer concentration in an artery to this area.

The build up rate ki and the blood flow rate fi are obtained from the partition coefficient λi obtained in this manner.

A preferred embodiment of the present invention will now be described with reference to the accompanying drawings.

Figure 1:
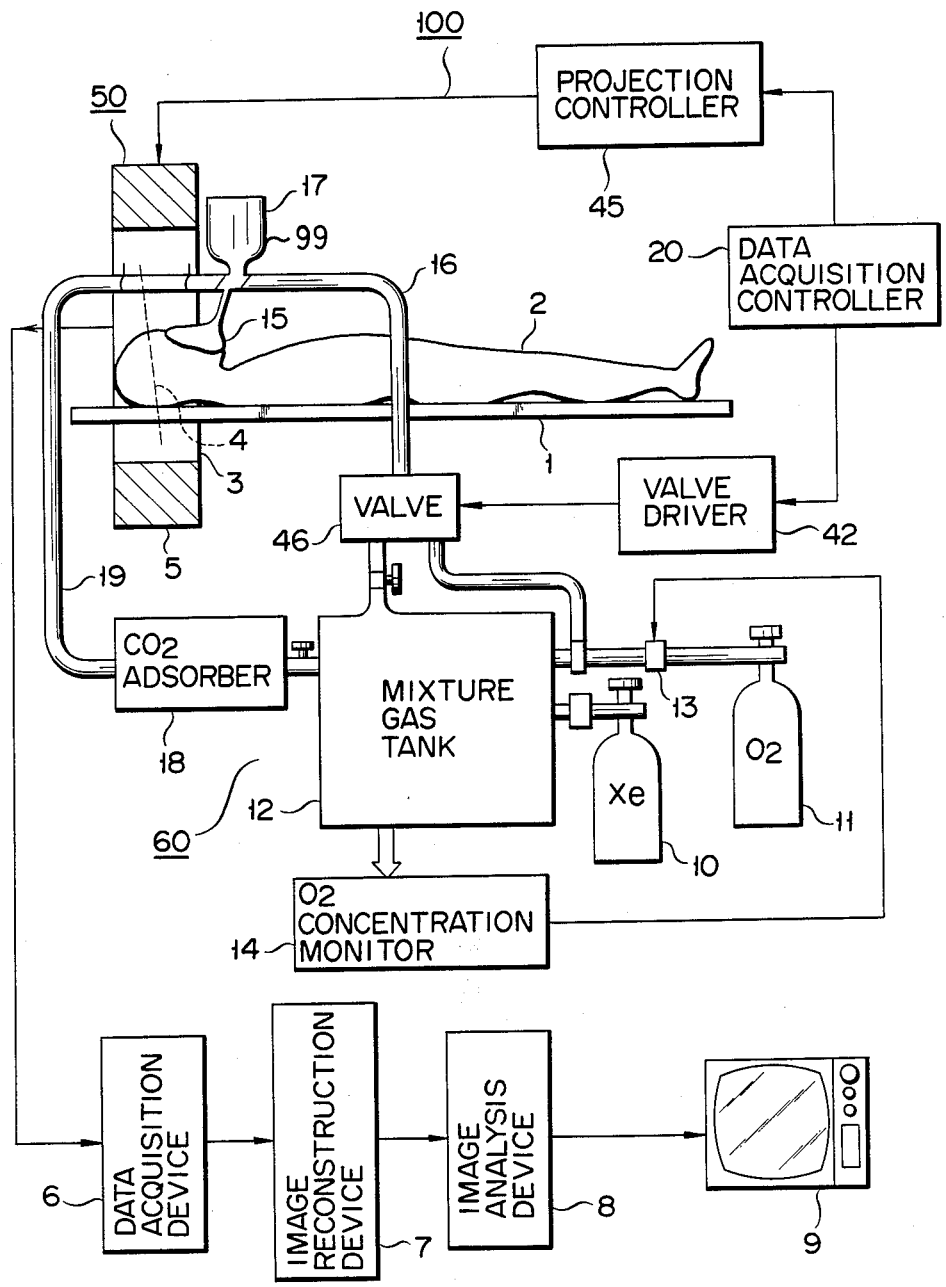
FIG. 1 is a schematic diagram of a CT imaging apparatus according to one preferred embodiment of the invention.

FIG. 1 is a block diagram showing the configuration of a CT imaging apparatus for measuring local cerebral blood flow according to an embodiment of the present invention. The apparatus 100 has an X-ray CT unit 50, a tracer inhalation unit 60, and a data acquisition control unit 20.

The X-ray CT unit 50 has a through hole 3 into which the head of a patient under examination, laying on a couch 1, can be placed. A gantry 5 obtains a tomographic image of a slice 4 by X-ray projection from an X-ray tube (not shown) pivoting around the head of the patient 2. A projection controller 45 instructs X-ray projection by controlling, for example, a high voltage applied to the X-ray tube in the gantry 5. A data acquisition device 6 acquires data from a detector (not shown) in the gantry 5 and obtains a number of projection data. An image reconstruction device 7 reconstructs a tomographic image of the slice 4 based on the projection data from the device 6. An image analysis device 8 analyzes tracer concentrations Ca(t) and Ci(t) based on the image data for a plurality of tomographic images of a programmed acquisition sequence from the device 7. A display device 9 displays the tomographic images obtained by the device 7 and/or the cerebral blood flow parameters λi, ki and fi from the device 8, and images representing the measured local cerebral blood flow.

The tracer inhalation unit 60 is a closed system so as to allow recovery and re-use of a tracer. A mixture gas tank 12 of the unit 60 mixes a tracer, e.g., Xenon gas supplied from a tracer reservoir 10 and oxygen from an oxygen reservoir 11. An oxygen concentration monitor 14 monitors the oxygen concentration in the tank 12. The monitor 14 automatically controls a gas-flow controlling valve 13 for adjusting the amount of oxygen supplied so as to maintain the oxygen concentration in the tank 12 at a predetermined level. A mask 15 covers the mouth and nose of the patient 2. A check valve 99 for supplying mixture gas to the inside of the mask 15 and for preventing the mixing of the expiratory gas of the patient 2 with the mixture gas is mounted at a portion of an expiratory tube 16 near the mask 15. The tube 16 is connected between the tank 12 and the mask 15. A gas-flow changing valve 46 for switching between the mixture gas and oxygen is driven by a valve driver 42. A buffer bag 17 is mounted on the mask 15 and buffers the mixture gas supplied through the tube 16. A check valve 99 for supplying the expiratory gas from the mask 15 to the tank 12 and for preventing reverse flows of the expiratory gas from the patient 2 is mounted at a portion of an expiration tracer gas tube 19 near the mask 15. The tube 19 is connected between the mask 15 and the tank 12 through a carbon dioxide gas adsorber 18 (to be described later). The adsorber 18 adsorbs and removes carbon dioxide gas in the expiratory gas.

A data acquisition controller 20 controls the X-ray projection timing through projection controller 45 and also controls the change timing between the mixture gas and oxygen through the valve driver 42.

A detailed configuration of the image analysis device 8 will be described with reference to FIG. 2.

FIG. 2 is a block diagram showing an example of the configuration of the device 8. Referring to FIG. 2, a first memory 21 stores image data (to be referred to as P(O) hereinafter) obtained from the device 7 before tracer inhalation begins (FIG. 1). A second memory 22 stores a plurality of image data (to be referred to as P(t) hereinafter) obtained from the device 7 after tracer inhalation begins. A subtraction device 23 performs subtraction of image data P(t)−P(O) stored in the memories 22 and 21, respectively. A third memory 25 stores tracer concentration in the expiration tracer gas in tube 19, Cair(t), supplied from the subtraction device 23 or tracer concentration in the expiration tracer gas, Cair(t), externally supplied through an external input terminal EXT1 in relation to time lapse. Either tracer concentration is stored in the third memory 25 by mode switching by a first switch 24. A fourth memory 26 stores a tracer concentration of tissue in relation to time lapse, Ci(t) (i=1, 2, ..., N) from the device 23. Note that i designates a predetermined voxel in the ROI (region of interest).

The device 8 further has an α calculation device 28. The device 28 calculates a conversion coefficient α of tracer concentration in blood based on an externally supplied Hematocrit value Ht(%). The conversion coefficient α is supplied to a Ca(t) calculation device 30 through a second switch 29.

The device 30 calculates the tracer concentration Ca(t) based on the conversion coefficient α supplied from the device 28 or a conversion coefficient α externally supplied through an external input terminal EXT2. The device 30 calculates by the following equation:

$$Ca(t) = \alpha \cdot Cair(t) \tag{3}$$

The conversion coefficient α from the device 28 or the externally supplied conversion coefficient α is selected by a mode switching of the second switch 29. A λi calculation device 31 calculates a partition coefficient λi based on the parameter Ca(t) from the device 30 and tracer concentration Ci(t) stored in the fourth memory 26. The device 31 calculates by the following equation:

$$\lambda i = \left( \int_0^{T2} Ci(t)dt \right) / \left( \int_0^{T2} Ca(t)dt \right) \tag{4}$$

A ki calculation device 33 calculates the build up rate Ki based on the parameter λi supplied from the device 31 or a partition coefficient λi externally supplied from an external input terminal EXT3, the tracer concentration from the fourth memory 26, and the tracer concentration Ca(t) from the device 30. The device 33 calculates by the following equation (5);

$$ki = (Ci(t) - Ci(T0))/\left(\lambda i \int_{T0}^{T} Ca(t)dt - \int_{T0}^{T} Ci(t)dt\right) \quad (5)$$

The partition coefficient λi from the device 31 or the partition coefficient λi externally supplied through the terminal ETX3 is used in accordance with mode switching of the third switch 32. An fi calculation device 33 calculates a parameter fi in accordance with the rate λi supplied to the device 33 and the build up rate ki supplied from the device 33. The device 34 calculates by the following equation:

$$fi = 100 \cdot \lambda i \cdot ki \, [\text{ml}/100 \, \text{g/min}] \quad (6)$$

The mode of operation of the X-ray CT apparatus 100 for measuring local cerebral blood flow and having the above configuration will be described below.

First, the valve 46 is switched from the oxygen side to the mixture gas side through the valve driver 42 under the control of the controller 20. Then, the mixture gas having a predetermined oxygen content controlled by the monitor 14 is supplied from the tank 12 to the patient 2 through the tube 16 and the mask 15. A tracer in the mixture gas is absorbed into the blood by the lungs of the patient 2, and the tracer carried by the blood is diffused into the brain tissue. The tracer circulated within the cerebral tissue is exhausted into the expiratory gas. The expiratory gas containing the tracer is supplied to the tube 19 and the adsorber 18 adsorbs carbon dioxide gas therefrom. The remaining gas is recovered into the tank 12, thereby forming a closed system for recovering the used tracer. It is understood from the foregoing that there is a direct proportion between the tracer concentration in the blood flowing in the blood vessels from the lungs to the heart and that of the gas in the inhalation tube.

Figure 3:
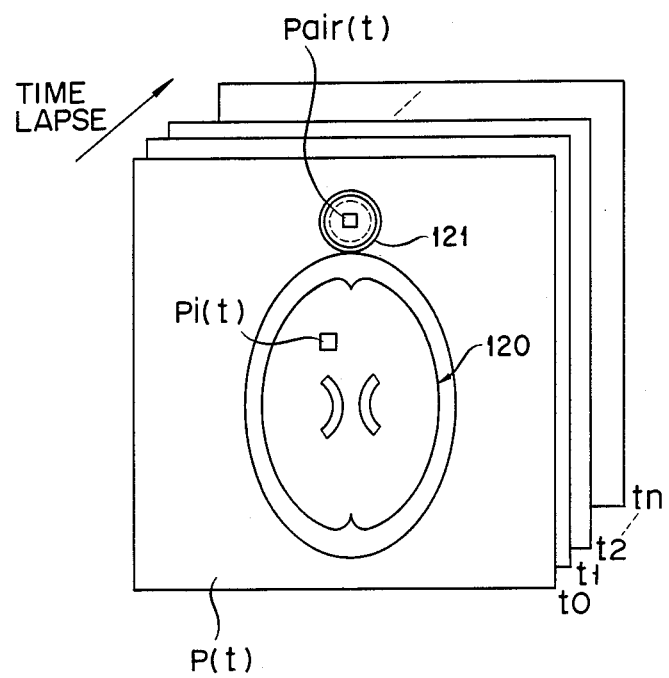
FIG. 3 is an illustration of tomographic images of a head and expiratory pipe taken by the apparatus shown in FIG. 1.

Substantially when the valve 46 is opened, X-ray projection from an X-ray tube (not shown) in the gantry 5 is started through the controller 45 under the control of the controller 20. Upon this X-ray projection, the tomographic examination of the slice 4 of the head of the patient 2 is started. Data output from the detector (not shown) in the gantry 5 is acquired as a number of projection data by the device 6. The projection data are obtained by one revolution of the X-ray tube through 360 degrees about the longitudinal axis of body of the patient 2 and are supplied to the device 7. The device 7 obtains images P(t) having the programmed time sequence t0, t1, ..., tn as shown in FIG. 3 which are reconstructed from the projection data. The images include a tomographic image 120 of the head of the patient 2 and a tomographic image 121 of the tube 19. Referring to FIG. 3, reference symbol Pair(t) denotes an average computerized tomographic (Ct) image; value at a time instance t when a circular or square ROI (region of interest) is set in the image 121 of the tube 19. Reference symbol Pi(t) denotes an average CT image value in a local tissue i(i=1, 2, ..., N) at time instance t in the image 20. The time sequence image data for images reconstructed by the device 7 is supplied to the device 8. The device 8 analyzes the tracer concentration Ca(t) of the artery and the tracer concentration Ci(t) of the local cerebral tissue.

Within a predetermined time period (4 to 6 minutes) from the start of supply of the mixture gas (tracer), the valve 46 is switched from the mixture gas side to the oxygen side through the valve driver 42. Thus, inhalation of the mixture gas by the patient 2 is stopped (tracer inhalation stop). However, X-ray projection under the control of the controller 20 is continued (for about 15 to 20 minutes from the starting of the data acquisition), thereby performing data acquisition.

The configuration of the image analysis device 8 will be described in detail with reference to the circuit diagram shown in FIG. 2.

First, the image data P(O) and P(t) before and after tracer inhalation is begun are supplied from the reconstruction device 7. The image data P(O) and P(t) are supplied to the subtraction device 23 through the first and second memories 21 and 22. Then, the subtraction device 23 performs a digital subtraction P(t)−P(O) and produces the tracer concentration Cair(t) in expiration tube 19 and the tracer concentration Ci(t) in the brain tissue. The tracer concentration Cair(t) is stored in the third memory 25 through the first switch 24, and the tracer concentration Ci(t) is stored in the fourth memory 26.

When the tracer concentration Cair(t) is measured using a mass spectrometer or the like, it can be externally supplied through the external input terminal EXT1 by operating the first switch 24.

Calculation of the coefficient α (conversion coefficient of the tracer concentration in blood) which is one characteristic feature of the present invention will be described.

The time-lapse variation of tracer concentration in an artery, Ca(t), can be expressed as a product of the time-lapse variation of the tracer concentration in expiration, Cair(t), and the conversion coefficient α of the tracer concentration in the blood.

Thus, it can be given by equation (3):

$$Ca(t) = \alpha \cdot Cair(t) \quad (3)$$

The conversion coefficient α can be measured by the following two methods in accordance with the method of measuring the tracer concentration Cair(t):

(A) Expiratory Tube Scanning Method

In this method, the Hematocrit value HT (%) in blood is measured to obtain the conversion coefficient α.

$$\alpha = 0.0011 \times Ht + 0.10 \quad (7)$$

In this case, the time-lapse variation of tracer concentration in expiration gas in tube 19, Cair(t) [H.U.], is obtained. The unit H.U. is a unit for CT values and stands for Hounsfield Unit.

(B) Mass Spectrometer Method

The Hematocrit value Ht (%) is measured, and the conversion coefficient α is calculated by the following equation:

$$\alpha = \{\rho\chi \times (0.0011 \times Ht + 0.10)\}/\{(\mu_\rho{}^w/\mu_\rho{}^x) \times 100\} \quad (8)$$

where $\rho\chi$: density of tracer $\chi$ (mg/cm$^3$); 5.15 (mg/cm$^3$) at 37° C. and 1 atm.

$\mu_p^w$: mass absorption coefficient of water $\mu_p^\chi$: mass absorption coefficient of tracer $\chi$ Note that the mass absorption coefficients of water and tracer $\chi$, $\mu_p^w$ and $\mu_p^\chi$, are constants determined by the CT apparatus used. Then, the volume % of the tracer concentration Cair(t) is calculated.

The above calculation of the conversion coefficient $\alpha$ is performed by the $\alpha$ calculation device 28.

When the conversion coefficient $\alpha$ is determined with the expiratory tube method, the tracer concentration Cair(t) can be converted into the tracer concentration Ca(t) by sampling only a small amount of blood for measurement of the Hematocrit value Ht (%). In particular, in the expiratory tube scanning method, since this conversion can be performed by only the Hematocrit value independently of ambient temperature and pressure and the type of CT apparatus used, high precision and easy operation are achieved.

The conversion coefficient $\alpha$ calculated by the device 28 is supplied to the device 30 through the second switch 29 and is used for calculating the tracer concentration Ca(t) by the equation (3). In this manner, the tracer concentration Ca(t) can be calculated without any substantial blood sampling. Note that the above description applies to the case wherein the expiratory tube scanning method (A) is adopted.

The conversion coefficient $\alpha$ can be externally supplied through the external input terminal EXT2 by the second switch 29.

FIG. 4 shows examples of the tracer concentration Ci(t) and the tracer concentration Ca(t) produced by the subtraction device 23 and calculation device 30 (although these values are obtained as discrete values, they are expressed in a continuous system for the sake of simplicity). Referring to FIG. 4, a time interval T0 to T1 is a tracer inhalation time period, and a time interval T0 to T2 is a data acquisition time period. The desirable parameters $\lambda i$, ki and fi are calculated in accordance with the two types of programmed acquisition sequence data, i.e., the tracer concentration of artery Ca(t) and the tracer concentration of local cerebral tissue Ci(t). The parameters $\lambda i$, ki and fi are calculated by the Kety-Schmidt equation (1) or (1') based on the Fick principle.

More specifically, the partition coefficient $\lambda i$ is calculated by the $\lambda i$ calculation device 31 by the equation (4). The calculated partition coefficient $\lambda i$ is supplied to the ki calculation device 33 through a third switch 32 and is used for calculating the build up rate ki.

The partition coefficient $\lambda i$ can be externally supplied through the external input terminal EXT 3 by operating the third switch 32. Each of white and gray matters has a predetermined partition coefficient $\lambda i$. Therefore, the partition coefficient $\lambda i$ externally supplied through the terminal EXT3 can be 0.8 to 1.0 for gray matter, 1.2 for 1.5 for white matter, and 1.0 as an average value for overall tissue. This allows simple, high-speed processing with small quantity of the acquired data.

The build up rate ki is calculated by the ki calculation device 33 by the equation (6). The analysis times T and T0 of the build up rate ki are set such that T0=0 and T=T1, or T0=T1 and T=T2. The former setting values correspond to the case of a rising portion ($0 \leq t \leq T1$) of the tracer concentration curve in FIG. 4, and the latter setting values correspond to the case of a falling portion ($T1 \leq t < T2$) of this curve. Therefore, the value of the build up rate ki in either portion can be used.

However, the S/N ratio can be improved if the values of the build up rate ki in both the portions are obtained, and the average value is used as the desired build up rate ki.

The blood flow rate fi is calculated by the fi calculation device 34 by the equation (6).

The parameters $\lambda i$, ki and fi calculated in this manner are displayed on the CRT display of the display device 9 in the form of numerical values or in images representing density patterns by luminance modulation. Images with functional information, such as local cerebral blood flow information, provide information additional to anatomic information such as a normal X-ray CT image, thus providing an advantage in the field of clinical examination.

Although the present invention has been described with reference to a particular embodiment thereof, the present invention is not limited to this embodiment and various other changes and modifications may be made within the spirit and scope of the present invention.

The CT imaging apparatus in the above embodiments is an X-ray CT imaging apparatus. However, the CT imaging apparatus according to the present invention can be selected from various CT imaging apparatuses such as NMR diagnostic apparatuses, single photon ECT apparatuses and positron apparatuses.

The data acquisition controller 20 in the above embodiments controls the X-ray projection timing and also the switching timing between the mixture gas and oxygen. However, the controller 20 can have any configuration provided that it can control the data acquisition timing at predetermined time intervals for a short period of time, i.e., from the inhalation of the mixture gas and hence inhalation of a tracer by the patient to exhaust thereof.

In particular, FIG. 2 only shows an example of details of the configuration of the image analysis device, and the configuration is not limited to this particular one.

The present invention has the following advantages.

The short tracer (mixture gas) inhalation time is controlled by the data acquisition controller. The rising and falling portions of a characteristic curve of the tracer concentration are measured to allow easy calculation of the cerebral blood parameters $\lambda i$, ki and fi.

Since a patient need to inhale a tracer for only a short period of time, the increase in the carbon dioxide gas concentration PaCO$_2$ and anesthetic effect of the patient are small, and precision of the obtained cerebral blood flow parameters is high.

The partition coefficient $\lambda i$ can be externally supplied as a constant or can be internally calculated by selection by means of the second switch 29 so as to allow selection between a high-speed simple method and a high-precision method.

In addition, since arterial blood sampling is not required, the measurement is essentially non-invasive and the load on the operator is decreased.

What is claimed is:

1. A CT imaging apparatus for measuring local cerebral blood flow of a patient under examination comprising:

a source of tracer gas;

a conducting member;

conducting member means for supplying tracer gas via the conducting member into the patient under examination;

means for controlling starting and ending times of supplying the tracer gas;

means, including at least an X-ray generation source, a data acquisition device and an image reconstruction device, for simultaneously producing X-ray tomographic image data of preselected slices in both the patient and the conducting member, said tomographic image data involving local cerebral blood flow in the patient and also tracer gas flow through the conducting member;

means for analyzing the tomographic image data involving the local cerebral blood flow and the tracer gas flow to measure the local cerebral blood flow and the tracer gas flow; and means for displaying a reconstructed tomographic image obtained from the tomographic image data and for displaying an image indicating the measured local cerebral blow flow.

2. A method for measuring local cerebral blood flow of a patient under examination comprising the steps of:

supplying tracer gas via a gas conducting member into a patient under examination;

controlling starting and stopping of the supplying of tracer gas to the patient;

simultaneously producing X-ray tomographic image data of preselected slices in both the patient and conducting member, said tomographic image data involving local cerebral blood flow in the patient and also tracer gas flow through said conducting member;

analyzing the tomographic image data involving the local cerebral blood flow and the tracer gas flow to measure the local cerebral blood flow and the tracer gas flow; and displaying a reconstructed tomographic image obtained from the tomographic image data and an image indicating the measured local cerebral blood flow.

3. The method of claim 2 wherein said step of analyzing includes the substep of obtaining a partition coefficient $\lambda i$ of a local cerebral portion i of the patient based upon the ratio of a first area, defined by a time-lapse variation curve of tracer gas concentration in a preselected volume of local cerebral tissue of the patient, to a second area, defined by a time-lapse variation curve of tracer gas concentration in an artery blood flow of the patient, said tracer concentration in said pre-selected volume of local cerebral tissue and in said artery blood flow being obtained from said tomographic image data.

4. The method of claim 3 wherein said substep of obtaining a partition coefficient $\lambda i$ further includes calculating said partition coefficient $\lambda i$ in accordance with the following equation:

$$\lambda i = \left[ \int_0^{T_2} C(t)dt \right] / \lambda i = \left[ \int_0^{T_2} Ca(t)dt \right], \text{ wherein}$$

$C_i(t)$ is tomographic image data representing tracer concentration in said pre-selected volume of local cerebral tissue, $C_a(t)$ is tomographic image data representing tracer concentration of said tracer gas flow through said conducting member; and $T_2$ is a data acquisition time period.

5. The method of claim 3 wherein said step of analyzing includes the additional substeps of selecting between said partition coefficient $\lambda i$ obtained by said step of obtaining and a partition coefficient $\lambda i$ externally supplied as a constant; and calculating the amount of blood flow $f_i$ based on said partition coefficient $\lambda i$ selected during said substep of selecting.

* * * * *